(12) United States Patent
Tobelem et al.

(10) Patent No.: US 8,916,144 B2
(45) Date of Patent: Dec. 23, 2014

(54) PROANGIOGENIC COMPOSITIONS, METHOD FOR PREPARING SAME, AND USES THEREOF

(75) Inventors: Gérard Tobelem, Paris (FR); Jean-Sébastien Silvestre, Sceau (FR)

(73) Assignees: Institut des Vaisseaux et du Sang (FR); Universite Paris Diderot Paris—7 (FR)

( * ) Notice: Subject to any disclaimer, the term of this patent is extended or adjusted under 35 U.S.C. 154(b) by 0 days.

(21) Appl. No.: 13/636,582

(22) PCT Filed: Mar. 28, 2011

(86) PCT No.: PCT/FR2011/050673
§ 371 (c)(1), (2), (4) Date: Nov. 13, 2012

(87) PCT Pub. No.: WO2011/117559
PCT Pub. Date: Sep. 29, 2011

(65) Prior Publication Data
US 2013/0058916 A1  Mar. 7, 2013

(30) Foreign Application Priority Data
Mar. 26, 2010  (FR) ..................... 10 52218

(51) Int. Cl.
| | |
|---|---|
| *C12N 5/078* | (2010.01) |
| *A61K 35/14* | (2006.01) |
| *A61P 9/10* | (2006.01) |
| *A61K 35/48* | (2006.01) |
| *A61K 35/28* | (2006.01) |
| *A61K 47/42* | (2006.01) |
| *A61K 38/17* | (2006.01) |
| *A61K 9/00* | (2006.01) |

(52) U.S. Cl.
CPC .............. *A61K 35/51* (2013.01); *A61K 35/15* (2013.01); *A61K 35/28* (2013.01); *A61K 47/42* (2013.01); *A61K 38/1793* (2013.01); *A61K 9/0019* (2013.01); *C07K 2319/30* (2013.01)
USPC .......................... 424/93.1; 514/13.3; 435/325

(58) Field of Classification Search
CPC .................... A61K 47/48415; C12N 5/0692
See application file for complete search history.

(56) References Cited

U.S. PATENT DOCUMENTS

2009/0123431 A1*  5/2009  Foubert et al. ............... 424/93.7

FOREIGN PATENT DOCUMENTS

| EP | 0 506 574 B1 | 9/1992 |
|---|---|---|
| EP | 2 047 859 A1 | 4/2009 |
| FR | 2 799 465 A1 | 4/2001 |
| FR | 2 799 549 A1 | 4/2001 |
| FR | 2 909 559 A1 | 6/2008 |
| WO | WO 02/092108 A1 | 11/2002 |
| WO | WO 2007/012764 A2 | 2/2007 |

OTHER PUBLICATIONS

International Search Report and Written Opinion dated Jul. 6, 2011 issued in corresponding international patent application No. PCT/FR2011/050673.
Foubert et al.: "PSGL-1-mediated activation of EphB4 increases the proangiogenic potential of endothelial progenitor cells", Journal of Clinical Investigation, American Society for Clinical Investigation, US LNKD-DOI: 10.1172/JCI28338, vol. 117, No. 6, Jun. 1, 2007, pp. 1527-1537, XP002439684, ISSN: 0021-9738.
Yang et al.: "Anti-aniogenic effects and mechanisms of polysaccharides from *Antrodia cinnamomea* with different molecular weights", Journal of Ethnopharmacology, Elsevier Scientific Publishers Ltd, IE, vol. 123, No. 3, Jun. 25, 2009, pp. 407-412, XP026150435, ISSN: 0378-8741.
Maekawa et al.: Ephrin-B2 Induces Migration of Endothelial Cells Through the Phosphatidylinositol-3 Kinase Pathway and Promotes Angiogenesis in Adult Vasculature, Arterioscler Thromb Vasc Biol. 2003 23(2):190-197.

* cited by examiner

*Primary Examiner* — Daniel C Gamett
(74) *Attorney, Agent, or Firm* — Ostrolenk Faber LLP

(57) ABSTRACT

The invention relates to novel proangiogenic compositions, to the method for preparing same, and to the uses thereof, particularly for preventing or treating any disease causing ischemic-type complications.

15 Claims, 2 Drawing Sheets

PROANGIOGENIC COMPOSITIONS, METHOD FOR PREPARING SAME, AND USES THEREOF

CROSS REFERENCE TO RELATED APPLICATIONS

The present application is a 35 U.S.C. §371 National Phase conversion of PCT/FR2011/050673, filed Mar. 28, 2011, which claims benefit of French Application No. 1052218, filed Mar. 26, 2010, the disclosures of which are incorporated herein by reference. The PCT international Application was Published in the French language.

BACKGROUND OF THE INVENTION

1. Technical Field

The present invention relates to novel proangiogenic compositions, to the method for preparing the same and to the uses, in particular therapeutic uses, thereof for preventing or treating any pathological condition causing ischemic-type complications.

The proangiogenic compositions of the invention open the way to novel cell therapy strategies.

In the description below, the references between square brackets [ ] refer to the list of references given at the end of the text.

2. Related Art

The demonstration of the existence of circulating endothelial progenitor cells (EPCs) and of their potential for use in stimulating angiogenesis and vascular repair is an important advance in the vascular biology field.

These cells can be present in the general circulation either spontaneously in response to various stimuli (pro-inflammatory cytokines, growth factors, ischemia, statins, etc.). These cells, which are involved in vascular repair mechanisms, open up an advantageous therapeutic route for the treatment of ischemic cardiovascular diseases.

Proangiogenic systems of the cell marker/specific ligand type comprising an endothelial progenitor cell comprising the Eph cell marker, in particular EphB4 or EphB1, have been described [1]. In such systems, in order to stimulate angiogenesis, the endothelial progenitor cells comprising the Eph marker are activated by a specific ligand belonging to the ephrin family. Endothelial progenitor cells can be obtained from mononuclear cells originating from the bone marrow, from peripheral blood or from umbilical cord blood. After differentiation, the mononuclear cells of the bone marrow or of the umbilical cord provide a relatively large amount of endothelial progenitor cells which express or comprise the Eph marker. In peripheral blood, there is a very small percentage of mononuclear cells which are circulating EPCs. However, the obtaining of endothelial progenitor cells via several steps (preselection and sorting by cytometry, ex vivo culture, differentiation and maturation of the cells, expansion) requires complex and lengthy manipulations; it is therefore expensive and has a low yield.

It is, moreover, known that the risk factors in cardiovascular diseases can induce vascular and cardiovascular disorders through endothelial dysfunction, said dysfunction possibly leading to a decrease in the number and in the function of the EPCs which are involved in tissue repair [2]. Dysfunction and a lower-than-normal amount of circulating EPCs have been observed in certain individuals with risk factors for cardiovascular diseases such as, for example, hypercholesterolemia, diabetes or hypertension [3].

There is therefore a real need to provide new compositions, which can stimulate angiogenesis at least with the same efficiency as the EPCs of various origins, or even the same intensity as angiogenic factors such as VEGF, and for these new compositions to comprise readily accessible cells not requiring by necessity:

a step of preselection and of sorting by cytometry, of ex vivo culture, of differentiation and/or maturation or to be in a mixture with other cells for stimulating angiogenesis.

There is also a real need to provide new compositions, capable of stimulating the angiogenesis function, comprising cells of which the number remains stable.

There is, in addition, a real need for new proangiogenic compositions, the use of which is easy, reproducible and inexpensive.

SUMMARY OF THE INVENTION

The purpose of the present invention is precisely to meet these needs by providing proangiogenic compositions comprising mononuclear cells (MNCs) originating from peripheral blood, and ligands L capable of bringing about the activation of said peripheral blood mononuclear cells (MNCs), in which the circulating blood mononuclear cells (MNCs) comprise receptors capable of receiving the ligands L in order to bring about the activation of said cells.

After activation by the ligands L, the circulating blood MNCs acquire proangiogenic properties comparable to or greater than those of EPCs originating from bone marrow or from umbilical cord blood.

For the purpose of the present invention, the expression "circulating blood mononuclear cells" is intended to mean mononuclear cells which have reached a state of maturation and are differentiated into monocytes and lymphocytes.

The term "peripheral blood" according to the invention is equivalent to the term "circulating blood".

Compared with EPCs, the mononuclear cells are more directly and more easily accessible since the isolation thereof, from circulating blood, does not require a step of preselection and of sorting by cytometry, of ex vivo culture, of differentiation and/or of maturation. This therefore facilitates the use of the proangiogenic compositions of the invention, but also can reduce the cost of production of said compositions.

In the case of pathological conditions requiring urgent treatments which cannot be delayed, the rapidity of access to the compositions according to the invention can constitute an important advantage.

The compositions of the invention avoid the problems associated with the transfusion of heterologous blood cells and constitute a promising approach. Indeed, the compositions according to the invention are suitable for use in autotransfusion.

Up until now, it had never been thought that circulating blood mononuclear cells (MNCs) can be activated directly in order to stimulate the proangiogenic activity. Moreover, the prior art teaches only proangiogenic compositions based on endothelial progenitor cells which result from differentiation of bone marrow mononuclear cells.

In the compositions according to the invention, the mononuclear cells (MNCs) can comprise receptors capable of receiving the ligands L in order to bring about the activation of said cells.

The compositions according to the invention can be in the form of a crude mixture of cells and molecules, of diverse natures and origins, and the properties of which can change or the number of which can increase, in order to have the MNCs in an amount sufficient for the use for which said composition is intended. The amount of mononuclear cells present in the composition and/or in the batch (or mixture) of cells to be used can be between, for example, $10^6$ and $10^{12}$.

The compositions according to the invention can also be in a "less crude" form, with certain cells and/or molecules removed by purification methods known to those skilled in the art. These methods must not be detrimental to the cells (MNCs). The "less crude" composition generally contains a higher concentration of cells (MNCs) capable of being stimulated, compared to the concentration of cells (MNCs) of the crude mixture. The amount of the cells present in the composition and/or in the batch (or mixture) of cells to be used can then be between, for example, $10^6$ and $10^{11}$ mononuclear cells.

The composition according to the invention can also comprise umbilical cord blood or bone marrow, or a mixture of both.

More particularly, the circulating blood mononuclear cells (MNCs) can originate from the peripheral blood of a mammal.

The term "mammal" denotes any mammal. By way of example, mention may be made of domestic animals such as dogs and cats; farm animals such as pigs, cattle, sheep and goats; animals such as mice and rats; primates such as monkeys and chimpanzees; and humans.

In the context of the present invention, "stimulating" the proangiogenic activity means causing an increase and an improvement in the proangiogenic properties in vitro and in vivo.

Still in the context of the invention, the term bringing about "the activation" of the circulating blood mononuclear cells (MNCs) denotes bringing about the initiation of a cell response on the part of the differentiating cells (MNCs).

As already indicated, the compositions according to the invention comprise circulating blood mononuclear cells (MNCs) comprising receptors capable of receiving the ligands L in order to bring about the activation of said cells. Even in the presence of an excess, the ligands L will bind only to the receptors capable of receiving them and not to all the receptors which may be present on the circulating blood mononuclear cells (MNCs).

The circulating blood mononuclear cells (MNCs) therefore comprise receptors capable of being stimulated by noncirculating membrane ligands, such as ephrins.

These receptors may, for example, be transmembrane receptor tyrosine kinases chosen from the group comprising EphAs and EphBs.

The ligands L may be ligands of the ephrin family. Ephrins can be divided up into two subfamilies, the type A ligands being simply bound to plasma membranes via a glycosylphosphatidylinositol (GPI) and the B ligands being transmembrane with an intracytoplasmic domain.

In one embodiment of the invention, the ligand L is a molecule with ephrin-B activity, more particularly a molecule with ephrin-B2 activity. The ligand L may be ephrin-B2.

The ligands L may be optionally associated with a stabilizing and/or bonding molecule. In the context of the present invention, the term "associated" covers any type of bond of different intensity and property: namely, covalent, ionic, polar, Van der Waals and hydrophobic. The stabilizing and/or bonding molecules can stabilize and/or protect the ligand. They can bind the ligand but cannot bind to the receptors.

In the compositions according to the invention, the stabilizing and/or bonding molecule may be, for example, an Fc fragment of an immunoglobulin. The Fc fragment, which results from the fragmentation of the peptide bonds of an immunoglobulin molecule, does not have an antigen-binding site. It does not therefore have antibody activity. The Fc fragment (or Fc domain) is the part of the immunoglobulin molecule that is formed by the constant regions of the two heavy chains. It is this Fc domain which gives the immunoglobulin its properties. The Fc fragment can be obtained from immunoglobulins, for example, via proteolytic action of papain, of pepsin or of any suitable enzyme.

Another subject of the invention is a proangiogenic material comprising circulating blood mononuclear cells (MNCs) activated by ligands L in order to stimulate angiogenesis, said ligands L being optionally associated with a stabilizing and/or bonding molecule.

In one embodiment of the invention, the proangiogenic material comprises circulating blood mononuclear cells (MNCs) stimulated by ephrin-B2 molecules as ligands, said ligands L being optionally associated with a stabilizing and/or bonding molecule. In this embodiment, said circulating blood mononuclear cells (MNCs) comprise receptors chosen from EphAs and EphBs, capable of being stimulated by ephrin-B2 molecules.

The invention also relates to the method for preparing a proangiogenic composition according to the invention, comprising the following steps:
(i) peripheral blood mononuclear cells (MNCs) are obtained and are placed in a suitable medium;
(ii) the mononuclear cells of step (i) are brought into contact with the ligands L,
said ligands being optionally associated with a stabilizing and/or bonding molecule.

The term "peripheral blood" according to the invention is equivalent to the term "circulating blood". The mononuclear cells originate from peripheral blood (PBMNCs).

In addition, the umbilical cord blood or the bone marrow, or a mixture of the two, can be added to the peripheral blood comprising the mononuclear cells of the step.

The MNCs can be isolated from peripheral blood by any suitable method known to those skilled in the art, for instance differential centrifugation, or sorting by flow cytometry.

The suitable medium of step (i) can be a physiological liquid comprising mainly water. The suitable medium may comprise at least 80%, advantageously 85% and even more advantageously at least 90% water.

In addition to the water, the suitable medium may comprise one or more elements chosen from:
  mineral solutes such as trace elements and ions, in particular $Na^+$, $Cl^-$, $K^+$, $PO_4^{3-}$, $C_a^{2+}$, $SO_4^{2-}$;
  organic solutes such as lipids, carbohydrates, amino acids, urea, uric acid, bilirubin, hormones;
  plasma proteins such as albumin, immunoglobulins, fibrinogen, lipoproteins, etc.

The suitable medium is more particularly a plasma.

In certain cases, the plasma may be autologous plasma.

The circulating blood mononuclear cells (MNCs) are brought into contact with ligands of the ephrin family.

The ligand L is advantageously a molecule with ephrin-B activity, more advantageously a molecule with ephrin-B2 activity. The ligand L in step (ii) may be ephrin-B2.

The ligand L may optionally be associated with a stabilizing/bonding molecule as previously described.

The mononuclear cells (MNCs) used comprise receptors capable of being stimulated by ligands of the ephrin family. These receptors can, for example, be transmembrane receptor tyrosine kinases chosen from the group comprising EphAs and EphBs.

The ligand L can optionally be associated with a stabilizing/bonding molecule as previously described.

The stabilizing/bonding molecule is advantageously an immunoglobulin Fc fragment.

In step (ii), the time during which the circulating blood mononuclear cells (MNCs) and the ligands L are brought into contact can be between 5 minutes and 6 hours, for example between 20 minutes and 4 hours, for example between 30 minutes and 1 hour.

The bringing into contact in step (ii) can be carried out at a temperature ranging from 20 to 50° C., for example between 25 and 40° C., for example 37° C.

The bringing into contact in step (ii) can be carried out in an atmosphere which promotes binding of the ligands L to the receptors of the circulating blood cells (MNCs), for example with $CO_2$ and oxygen percentages ranging respectively between 2% and 10%, and between 98% and 90%, the sum of the $CO_2$ and oxygen percentages being equal in all cases to 100%. More particularly, the atmosphere chosen is composed of 5% $CO_2$ and 95% oxygen.

In the method of the invention, a washing step can also be carried out after step (ii). The washing could be carried out with a suitable medium as previously described.

The invention also extends to the proangiogenic compositions which can be obtained according to the method of the invention, said composition comprising circulating blood mononuclear cells (MNCs) and ligands L capable of activating said circulating blood mononuclear cells (MNCs) in order to stimulate the proangiogenic activity;

said ligands L being optionally associated with a stabilizing and/or bonding molecule.

The proangiogenic compositions according to the invention can be used directly or in the form of a pharmaceutical composition, for use as a medicament.

The proangiogenic material according to the invention can also be used directly or in the form of a pharmaceutical composition containing it, for use as a medicament.

Thus, one of the aspects of the invention may be the proangiogenic composition or the proangiogenic material, according to the invention, for use thereof as a medicament, in particular for the treatment and regeneration of vascular tissues which have been damaged, in particular at the cardiac, cerebral or else peripheral level; or in therapy, in particular for the prevention or treatment of any pathological condition causing ischemic complications, such as diabetes, diabetic neuropathy, atherosclerosis, myocardial infarction, strokes, lower limb arteriopathy, ageing, hyperlipidemia, hypercholesterolemia, obesity or hypertension.

According to another of its aspects, the present invention relates to pharmaceutical compositions comprising a proangiogenic composition or a proangiogenic material, according to the invention, and optionally one or more pharmaceutically acceptable excipient(s).

The pharmaceutical compositions according to the invention can be prepared by known methods.

The excipients are usually elements with no therapeutic activity which form part of the composition of a medicament or which are used for the production thereof. The function of the excipient is to improve the appearance, to ensure storage, and to facilitate the forming and the administration of the medicament. It also serves to convey the active ingredient to its site of action and to control its absorption by the organism. Depending on the pharmaceutical form and the mode of administration desired, various excipients can be used. Those skilled in the art are able to select the appropriate excipients according to the pharmaceutical form and the mode of administration desired [6].

The amount of proangiogenic composition of or proangiogenic material directly administered or included in the pharmaceutical compositions is a therapeutically effective amount. The term "effective amount" or "therapeutically effective amount" is intended to mean an amount of proangiogenic composition, of proangiogenic material or of pharmaceutical composition which produces the desired prophylactic or therapeutic effect. Said effective amount can be determined experimentally by means of standard pharmaceutical procedures.

In order to obtain the desired therapeutic effect, the dose of active ingredient (for example, ephrin B2-Fc) necessary for activating the cells can range between 10 and 200 micrograms per ml, and the number of activated cells in the batch to be used is from $10^8$ to $10^{11}$ cells per treatment. Although these dosages are examples of an average situation, there may be particular cases where higher or lower dosages are appropriate. Such dosages are part of the invention. According to the usual practice, the dosage appropriate for each patient is determined by the physician according to the mode of administration and the weight and response of said patient.

The mode of administration can be advantageously parenteral. The parenteral administration can comprise, for example, intravenous, intramuscular, subcutaneous, intraperitoneal, intra-arterial, intra-articular, intra-cisternal, intradermal, intralesional, intraocular, intrapleural, intrathecal, intrauterine and intraventricular administration. The therapeutic indication to be treated and also the physiochemical and biological properties of the composition make it possible to determine the route of administration and the formulation which are the most appropriate. Various formulations and administration systems are described in the prior art [5].

The proangiogenic compositions or the proangiogenic materials, of the invention, can be used for the production of a medicament intended for the treatment and for the regeneration of vascular tissues which have been damaged, in particular at the cardiac, cerebral or else peripheral level. They can also be used for the production of a medicament intended for the prevention or treatment of any pathological condition causing ischemic complications, such as diabetes, diabetic neuropathy, atherosclerosis, myocardial infarction, strokes, lower limb arteriopathy, ageing, hyperlipidemia, hypercholesterolemia, obesity or hypertension.

According to one of its aspects, the present invention relates to a proangiogenic composition or a proangiogenic material, according to the invention, for the treatment and regeneration of vascular tissues which have been damaged, in particular at the cardiac, cerebral or else peripheral level.

According to another of its aspects, the present invention relates to a proangiogenic composition or a proangiogenic material, according to the invention, for the prevention or treatment of any pathological condition causing ischemic complications, such as diabetes, diabetic neuropathy, atherosclerosis, myocardial infarction, strokes, lower limb arteriopathy, ageing, hyperlipidemia, hypercholesterolemia, obesity or hypertension.

The invention also relates to the use of a molecule with ephrin-B2 activity as a ligand capable of binding to the receptors of mononuclear cells (MNCs) in order to trigger activation thereof.

The proangiogenic compositions of the invention can be used in cell therapy in mammals and in particular in humans.

According to another of its aspects, the present invention also relates to a method for preventing or treating the pathological conditions indicated above, which comprises the administration of a proangiogenic composition or of a pharmaceutical composition comprising it, of a proangiogenic material or of a pharmaceutical composition comprising it.

A first method can consist in:
isolating the mononuclear cells (MNCs) from circulating blood and/or from bone marrow;
activating the MNCs in vitro by binding of the ligands L to their specific receptors present on the MNCs, in order to improve their proangiogenic property; and
introducing the cells (MNCs) thus activated into the blood or directly into the ischemic tissues.

This method makes it possible to significantly increase the number of activated cells (MNCs). The in vitro activation of the MNCs can also be useful for seeding vascular prostheses for example.

A second method can consist in:
directly using a blood and/or bone marrow sample in its entirety, containing cells (MNCs) optionally with other cells and cytokines;
adding ligands L to said sample;
directly introducing the whole mixture without cell fractionation.

In humans, this method may be described as autologous and makes it possible to carry out autotransfusions, thereby making it possible to eliminate, for example, all the problems of immunological compatibility and of viral safety.

DESCRIPTION OF PREFERRED EMBODIMENTS

Methods and Materials

Figure 1:
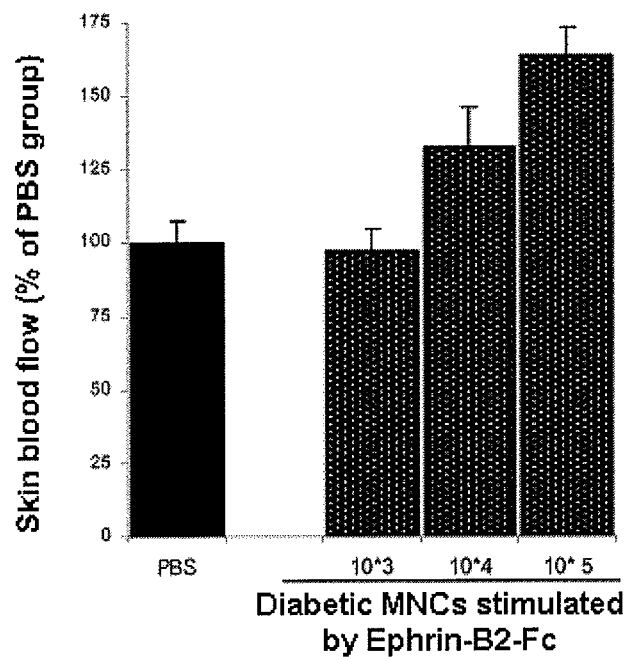
FIG. 1 represents the results of mouse ischemic and nonischemic leg skin perfusion, evaluated by laser-Doppler perfusion imaging velocimetry (MLDI 5078, sold by the company Moon instruments).

The experiments are carried out in accordance with the legislation protecting animals in the context of animal experimentation and any other law or regulation in force in France and in accordance with the European Community Directive No. 07430 relating to the care and use of laboratory animals. The study protocols are approved by the Department of Animal Protection and Health and Protection of the Environment, Ministry of Agriculture, France.

Example 1

Preparation of a Proangiogenic Composition According to the Invention

MNC Isolation 30 to 40 ml of human peripheral blood were freshly collected in heparin-coated tubes (Vacuette 455051, sold by the company Greiner Bio-One GmbH). The mononuclear cells (MNCs) were isolated from peripheral blood by Ficoll density gradient centrifugation. Two hours before the intravenous (iv) injection of the cells (MNCs) into the animals, the blood samples were diluted two-fold with phosphate buffered saline or PBS (14040 sold by the company Gibco). 30 to 35 ml of the diluted blood sample were placed as a layer on 10 ml of a previously prepared band of Ficoll (1.077 g/ml; P04-60500 sold by the company Pan Biotech). The centrifugation was carried out at ambient temperature (approximately 20° C.) for 30 minutes at 700×g (or 700 times the acceleration of gravity). The white layer of cells (MNCs) was removed from the plasma-Ficoll interface. After two washes with 50 ml of M199 (31153 sold by the company Gibco), the mononuclear cells were counted and resuspended in an M199 medium containing 2% fetal bovine serum or FBS at a concentration of $3 \times 10^6$ cells/ml.

MNC Stimulation

For the stimulation, $3 \times 10^6$ mononuclear cells (MNCs) in 1 ml of M199 medium containing 2% fetal bovine serum or FBS were incubated with 15 µg of ephrin-B2 (496-EB, R&D Systems) at 37° C. for 30 minutes under an atmosphere containing 5% $CO_2$ and 95% oxygen. The stimulated cells (MNCs) were then washed twice with 10 ml of M199 medium containing 2% FBS in order to remove the free ephrin-B2.

MNC Injection

The washed MNCs were resuspended at a concentration of $10^3$, $10^4$ and $10^5$ cells per 100 µl of PBS and then injected into the tail vein of the mice operated upon, hours after ligature of the femoral artery under sterile conditions.

Example 2

Proangiogenic Activity of the Compositions According to the Invention

Preparation of Athymic Nude Mice

Male athymic nude adult mice (6 to 7 weeks old, Harlan) were housed with free access to food and water, for at least 7 days before ligature of the right femoral artery. The mice were kept on an inverted 12 h night/day cycle: the mice are kept in the dark from 7 am to 7 pm and then in light from 7 pm to 7 am, at ambient temperature (22° C.). All the manipulations are carried out under pathogenic-microorganism-free conditions. The mice were kept in disposable plastic cages comprising filters in their upper part. The cage, the upper filter part, the water bottle, the feeder tray (Innovive) and the chow feed (Harlan) were UV-irradiated beforehand. The drinking water was treated in an autoclave prior to its use.

Ligature of the Right Femoral Artery

A surgical procedure was carried out in order to create a unilateral ischemia of the hind leg under sterile conditions. The mice were anesthetized by inhalation of isoflurane (1.5 to 2.0%). The leg withdrawal reflex and the eye blinking reflex were completely suppressed before the procedure. The femoral artery was exposed by making an incision in the central part of the overlying skin of the right leg. Using a microscope, the femoral artery was dissected and separated from the vein, just above the starting point of the circomflexa femoris lateralis. The overlying skin was then closed using a surgical stapler.

Leg Skin Perfusion Evaluation

Evaluation of the skin blood flow of the leg via ephrin-B2-stimulated cells (MNCs) makes it possible to evaluate the capacity of the stimulated cells (MNCs) to improve the perfusion of the limb rendered ischemic.

On day 14 post-ligature, the animals were anesthetized by intraperitoneal (ip) injection of pentobarbital (10 mg/kg). The mice were then placed on a heating blanket and the rectal temperature was maintained between 36.5 and 37° C. in order to minimize the influence of body temperature on the leg skin perfusion. Evaluation was then carried out by means of a perfusion imaging Doppler laser (MLDI 5078, sold by the company Moon Instruments). The skin perfusion results for each animal were expressed as a ratio of the right leg rendered ischemic versus the left leg not rendered ischemic.

Arterial Density Determination

Determination of the vascular density via ephrin-B2-stimulated cells (MNCs) makes it possible to evaluate the capacity of said stimulated cells to induce remodeling of the pre-existing vascular network (vascular remodeling).

Following the leg skin perfusion evaluation, the vascular density was determined by high-definition microangiography (2200, sold by Kodak Dental Systems, France). A longitudinal laparotomy was performed and a polyethylene (PE-10) catheter was inserted into the abdominal aorta through which approximately 150 µl of contrast product (1.67 g/ml of barium sulphate in saline) (Fluka-11845, sold by the company Sigma, France) were injected. The microangiography of the hind leg was then established and the images (2 to 3 images per animal) were acquired by means of a digital X-ray transducer. The arterial density of each hind leg was estimated as a percentage of pixels per image in the region of quantification occupied by arteries using conventional quantitative image analysis. The vascular density results for each animal were expressed as a ratio of the right leg (rendered ischemic) versus the left leg (not rendered ischemic).

For the immunohistochemical analysis, the twin triceps muscles of all the animals were collected, embedded in a Tissue-Tek O.C.T. matrix (sold by the company Finetek Europe) and rapidly frozen using isopentyl precooled in liquid nitrogen.

Capillary Density Quantification

Quantification of the capillary density via ephrin-B2-stimulated cells (MNCs) makes it possible to evaluate the capacity of said stimulated cells to induce the development of the vascular system from a capillary network (vasculogenesis and/or angiogenesis).

For the evaluation of the capillary density, each frozen muscle sample is sectioned using a cryostat (sold by the company Leica). The sections are 7 µm thick. The sectioning was carried out at three different levels of the sample, separated by a distance of approximately 300 µm. The sections were incubated for one hour at ambient temperature (20° C.) with fluorescein isocyanate or FITC conjugated to isolectin B4 (100 µl per slide, 10 µg/ml; L2895 sold by the company Sigma).

Using a fluorescence microscope equipped with appropriate filters (Observer ZI, sold by the company Zeiss), six images, (two images per level×three levels) were acquired for each ischemic or nonischemic muscle sample. The HistoLab software (version 7.0, sold by the company Microvision Instrument) was used in order to quantify the capillary density. The results for each animal were expressed as a ratio of capillary density in the rear leg rendered ischemic versus the rear leg not rendered ischemic.

Statistical Analyses

The leg skin perfusion, arterial density and capillary density results are expressed as a mean percentage of the control group treated with PBS (phosphate buffered saline)±SEM (standard error of the mean). The comparisons between the various experimental groups were carried out by means of a one-way analysis of variance (ANOVA) followed by a supplementary analysis by means of Fischer's PLSD method (Fischer's Protected Least Significant Difference Method). The P values below the 0.05 significance threshold (P<0.05) were considered to be significant.

Effects of Circulating Blood Cells (MNCs) Stimulated with Ephrin-B2 (EFNB2) on Post-Ischemic Revascularization Leg Skin Perfusion The cells (MNCs) originating from the venous blood of diabetic patients, stimulated with EFNB2, at cell concentrations of $10^3$, $10^4$ and $10^5$, significantly modified the skin perfusion of the legs in comparison with PBS on day 14 post-ischemia (97±7%, 132±14% and 163±10% of the PBS group for MNCs stimulated with EFNB2 at $10^3$, $10^4$ and $10^5$ cells, respectively, FIG. 1).

Angiography Result

Figure 2:
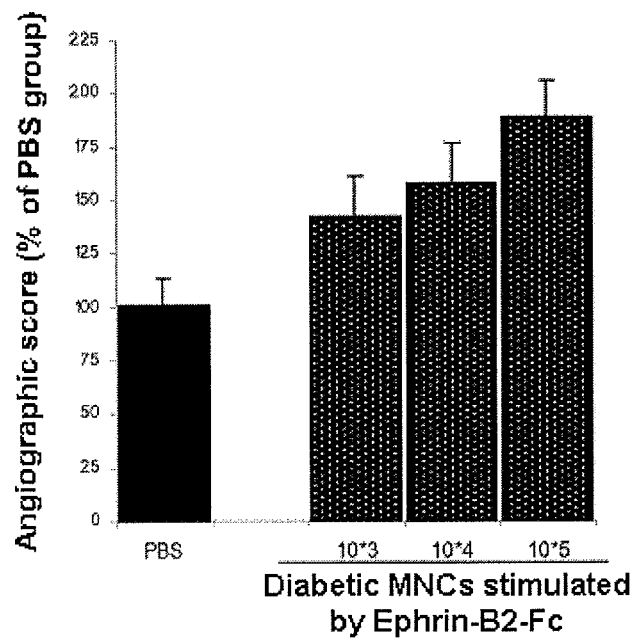
FIG. 2 represents the mouse ischemic and nonischemic leg angiographic score results evaluated by high-definition microangiography (2200, sold by Kodak Dental Systems, France).

The angiographic score is significantly increased by the MNCs originating from diabetic patients, stimulated with EFNB2, at cell concentrations of $10^3$, $10^4$ and $10^5$, compared with PBS at day 14 post-ischemia (142±19%, 157±19% and 189±17% of the PBS group for MNCs stimulated with EFNB2 at $10^3$, $10^4$ and $10^5$ cells, respectively, FIG. 2).

Capillary Density

Figure 3:
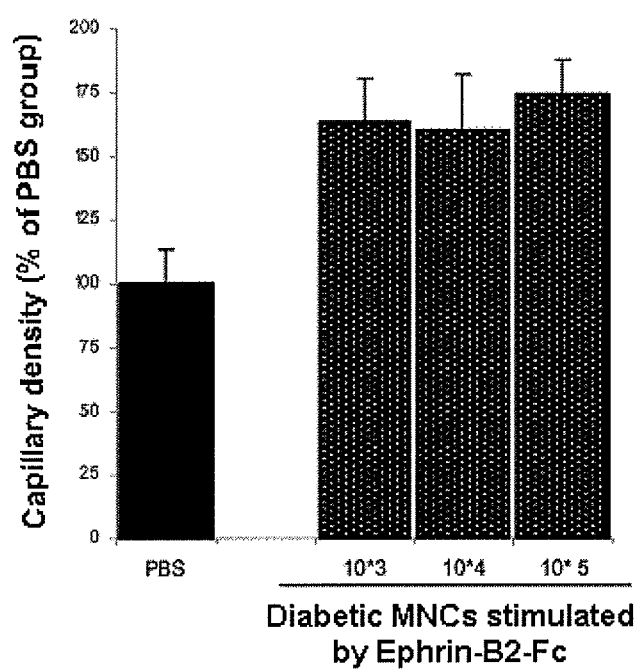
FIG. 3 represents the results of capillary density in mouse ischemic and nonischemic leg muscles, evaluated by quantitative immuno-histomorphometry (Leitz fluorescence microscope and Histolab software sold by Microvision (Evry)).

At day 14 post-ligature, the intravenous delivery of the MNC cells stimulated with EFNB2, at cell concentrations of $10^3$, $10^4$ and $10^5$, significantly increased capillary density (163±14%, 156±11% and 171±23% of the PBS group for MNCs stimulated with EFNB2 at $10^3$, $10^4$ and $10^5$ cells, respectively, FIG. 3).

In conclusion, the diabetic-patient peripheral blood mononuclear cells activated with ephrin-B2-Fc have a beneficial proangiogenic effect which is very marked from the functional point of view (skin blood flow measurement) and from the structural point of view (arterial microangiography and capillary density measurements).

REFERENCE LIST

[1] WO 2007/012764.
[2] Quyyumi et al., Can. J. Cardio. 20, 44B-8B, 2004;
[3] Vasa et al., Circ. Res. 89, E1-7, 2001.
[3] Verma et al., Circulation, 105, 546-549, 2002; Vasa et al. Circ. Res. 89, c1-c7, 2001; Tepper et al., Circulation, 106, 2781-2786, 2002.
[4] Iba et al., Circulation, 2019-2025, 2002.
[5] Gennaro ed. (2000) Remington's Pharmaceutical Sciences; Hardman, Limbird and Gilman, eds. (2001) The Pharmacological Basis of Therapeutics.
[6] Pharmacopeias USP, JP, EP; A. Le Hir, J-C. Chaumeil, D. Brossard, Pharmacie galénique [Galenical pharmacy], 9th edition, p. 36-93, 2009.

What is claimed is:

1. A proangiogenic composition, formed by a process comprising:
   (i) obtaining peripheral blood mononuclear cells (MNCs) having receptors selected from the group comprising of EphAs and EphBs;
   (ii) placing the peripheral blood mononuclear cells (MNCs) in a suitable medium; and
   (iii) activating the peripheral blood mononuclear cells (MNCs) placed in the suitable medium by contact with ephrin-B which is associated with at least one of a stabilizing and a bonding molecule in order to stimulate the proangiogenic activity of said peripheral blood mononuclear cells (MNCs).

2. The composition as claimed in claim 1, further comprising umbilical cord blood or bone marrow, or a mixture of the two.

3. The composition as claimed in claim 1, wherein the ephrin-B comprises ephrin-B2.

4. The composition as claimed in claim 1, wherein the at least one of a stabilizing molecule and a bonding molecule comprises an immunoglobulin Fc fragment.

5. A pharmaceutical composition comprising a proangiogenic composition according to claim 1.

6. A method for prevention or treatment of a pathological condition which causes ischemic-type complications, selected from the group consisting of one or more of diabetes, diabetic neuropathy, atherosclerosis, myocardial infarction, strokes, lower limb arteriopathy, hyperlipidemia, hypercholesterolemia, obesity and hypertension, comprising administering the proangiogenic composition according to claim 1.

7. A method for anti-aging comprising a step of administering the proangiogenic composition as claimed in claim 1.

8. A pharmaceutical composition comprising a proangiogenic material as claimed in claim 1 and optionally one or more pharmaceutically acceptable excipient(s).

9. A method for preparing a proangiogenic composition, comprising the following steps:
   (i) obtaining peripheral blood mononuclear cells (MNCs) and placing the peripheral blood mononuclear cells (MNCs) in a suitable medium; and
   (ii) activating the peripheral blood mononuclear cells (MNCs) placed in the suitable medium by bringing by contact with ephrin-B which is associated with at least one of a stabilizing and a bonding molecule in order to stimulate the proangiogenic activity of said peripheral blood mononuclear cells (MNCs).

10. The method as claimed in claim 9, in which umbilical cord blood or bone marrow, or a mixture of the two, is added to the peripheral blood mononuclear cells in the suitable medium.

11. The method as claimed in claim 9, wherein the suitable medium is plasma.

12. The method as claimed in claim 9, wherein the ephrin-B is ephrin-B2.

13. The method as claimed in claim 9, further comprising administering the proangiogenic composition to a human for prevention or treatment of a pathological condition which causes ischemic-type complications, selected from the group consisting of one or more of diabetes, diabetic neuropathy, atherosclerosis, myocardial infarction, strokes, lower limb arteriopathy, hyperlipidemia, hypercholesterolemia, obesity and hypertension.

14. The method as claimed in claim 9, wherein the at least one of a stabilizing molecule and a bonding molecule comprises an immunoglobulin Fc fragment.

15. A method for triggering activation of peripheral blood mononuclear cells (MNCs) comprising providing ephrin-B2 activity in a medium containing the peripheral blood mononuclear cells (MNCs) as a ligand capable of binding to receptors of the peripheral blood mononuclear cells (MNCs) to trigger activation of the peripheral blood mononuclear cells (MNCs).

* * * * *